(12) United States Patent
Primavera et al.

(10) Patent No.: US 8,398,679 B2
(45) Date of Patent: Mar. 19, 2013

(54) MODULAR SUTURE

(75) Inventors: Michael Primavera, Orange, CT (US);
Gregory G. Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 132 days.

(21) Appl. No.: 12/914,214

(22) Filed: Oct. 28, 2010

(65) Prior Publication Data
US 2012/0109193 A1  May 3, 2012

(51) Int. Cl.
*A61B 17/04* (2006.01)
(52) U.S. Cl. ........................................................ 606/228
(58) Field of Classification Search ................. 606/151, 606/213, 224–227, 228–232
See application file for complete search history.

(56) References Cited

U.S. PATENT DOCUMENTS

| | | | |
|---|---|---|---|
| 1,757,129 A * | 5/1930 | McClure | 606/225 |
| 1,960,117 A * | 5/1934 | Lydeard | 606/225 |
| 2,240,330 A * | 4/1941 | Flagg et al. | 606/225 |
| 2,591,063 A | 4/1952 | Harry | |
| 3,880,167 A | 4/1975 | Hardwick | |
| 4,155,125 A | 5/1979 | Woodcock et al. | |
| 4,182,341 A | 1/1980 | Perri | |
| 4,981,149 A | 1/1991 | Yoon | |
| 5,041,128 A | 8/1991 | Korthoff | |
| 5,051,107 A | 9/1991 | Korthoff | |
| 5,059,212 A | 10/1991 | Korthoff | |
| 5,067,959 A | 11/1991 | Korthoff | |
| 5,084,063 A | 1/1992 | Korthoff | |
| 5,089,010 A | 2/1992 | Korthoff | |
| 5,089,011 A | 2/1992 | Korthoff | |
| 5,102,418 A | 4/1992 | Granger et al. | |
| 5,116,358 A | 5/1992 | Granger | |
| 5,123,911 A | 6/1992 | Granger et al. | |
| 5,129,558 A | 7/1992 | Feuerman | |
| 5,133,738 A | 7/1992 | Korthoff et al. | |
| 5,139,514 A | 8/1992 | Korthoff et al. | |
| 5,156,615 A | 10/1992 | Korthoff et al. | |
| 5,226,912 A | 7/1993 | Kaplan et al. | |
| 5,259,845 A | 11/1993 | Korthoff | |
| 5,259,846 A | 11/1993 | Granger et al. | |
| 5,280,674 A | 1/1994 | Granger et al. | |
| 5,306,288 A | 4/1994 | Granger et al. | |
| 5,403,345 A | 4/1995 | Spingler | |
| 5,931,855 A * | 8/1999 | Buncke | 606/224 |
| 5,961,539 A * | 10/1999 | Northrup et al. | 606/232 |
| 5,972,024 A * | 10/1999 | Northrup et al. | 606/232 |
| 6,190,401 B1 * | 2/2001 | Green et al. | 606/224 |
| 6,296,659 B1 | 10/2001 | Foerster | |
| D467,726 S | 12/2002 | Zaniewski et al. | |
| 6,960,221 B2 | 11/2005 | Ho et al. | |
| 7,588,594 B2 * | 9/2009 | Sander et al. | 606/224 |
| 7,722,643 B2 | 5/2010 | Schaller et al. | |
| 2006/0135994 A1 | 6/2006 | Ruff et al. | |
| 2008/0154286 A1 | 6/2008 | Abbott et al. | |
| 2010/0160961 A1 | 6/2010 | Nawrocki et al. | |

FOREIGN PATENT DOCUMENTS

EP  2 108 316 A1  10/2009
WO  WO 02/080780 A1  10/2002

OTHER PUBLICATIONS

European Search Report for EP 11250772.8-2310 date of completion is Jan. 9, 2012 (3 pages).

* cited by examiner

*Primary Examiner* — Julian Woo

(57) ABSTRACT

Sutures are provided having a first elongate body and a separate, second elongate body. The first elongate body includes a first connection structure and the second elongate body may include a second connection structure.

16 Claims, 6 Drawing Sheets

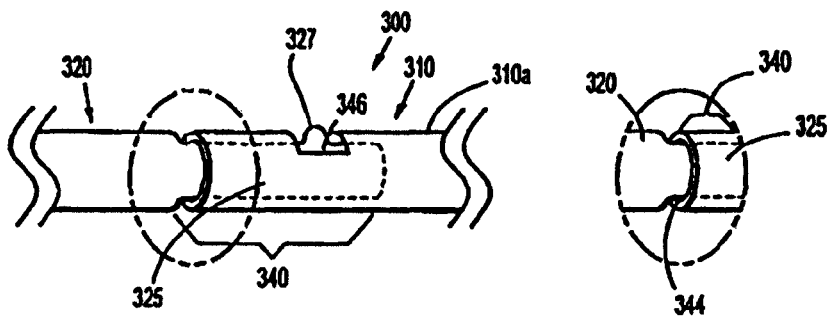
FIG. 3
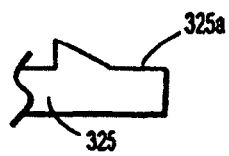    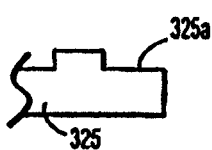    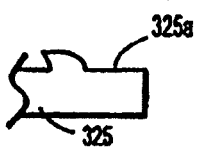    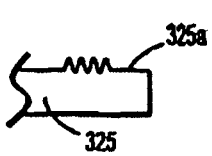
FIG. 4A    FIG. 4B    FIG. 4C    FIG. 4D
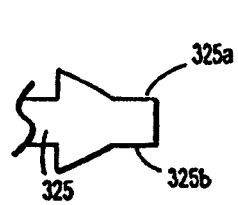    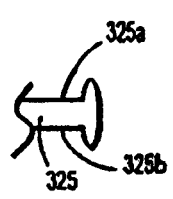    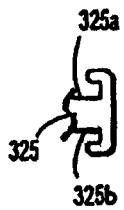    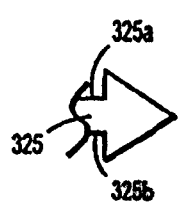
FIG. 4E    FIG. 4F    FIG. 4G    FIG. 4H
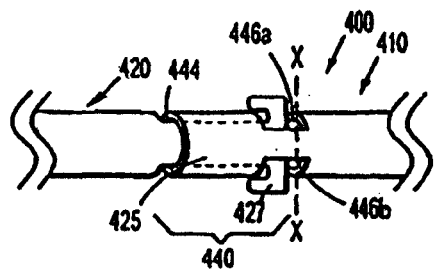    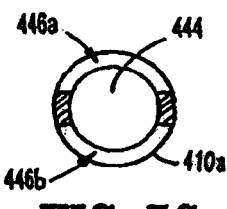
FIG. 5B    FIG. 5C
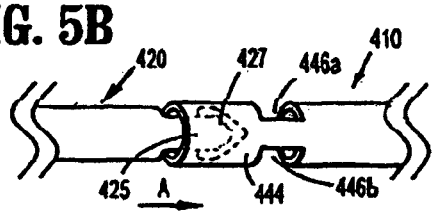
FIG. 5A

MODULAR SUTURE

BACKGROUND

1. Technical Field

The present disclosure describes sutures having connection structures which enable various lengths and configurations of sutures to be created.

2. Background of Related Art

Medical sutures may be formed from a variety of materials and may be configured for use in limitless applications. Sutures are provided in various lengths and typically have a needle attached to at least one end thereof. Barbed sutures are also known, the barbs may comprise a single direction, e.g., monodirectional barbed suture or two directions, e.g., bidirectional barbed suture. In certain situations, it may be preferable for the user to choose a different suture configuration.

SUMMARY

The present disclosure is direct to a suture comprising a first elongate body having a first connection structure; and a separate second elongate body selectively connectable to the first connection structure. In certain embodiments, the second elongate body comprises an extension projecting therefrom, the extension being selectively connectable to the first connection structure. The extension may comprise tabs or projections and the first connection structure comprises slots shaped to receive the tabs or projections. The tabs or projections may lock into the slots upon insertion of the extension into the first elongate body and in alternate embodiments, removal of the second elongate body is prevented.

The second elongate body may comprise a second connection structure. The first connection structure may be shaped to receive the second connection structure. In particular embodiments, the first connection structure is releasably connected to the second connection structure. The first or second connection structure may be selected from the group consisting of a ball connection, a socket connection, a threaded connection, and a flared connection. More specifically, the first and second connection structures may form a snap fit connection. In some embodiments, the first connection structure comprises a cavity.

The first or second elongate body may further comprise barbs disposed on a length thereof.

The first or second elongate body may comprise an end effector selected from the group consisting of a loop and a knot.

Further, the first or second elongate body may comprise a needle disposed at one end thereof.

According to another embodiment of the present disclosure, a suture comprising at least two separately connectable elongate bodies, wherein a first elongate body comprises an end portion including a first connection structure that is connectable to a second connection structure of a second elongate body is disclosed. The first elongate body may comprise a first plurality of barbs wherein the first plurality of barbs may prevent suture reversal in a first direction. The second elongate body may comprise a second plurality of barbs and the second plurality of barbs may prevent suture reversal in a second direction.

BRIEF DESCRIPTION OF THE DRAWING

These and other characteristics of the present invention will be more fully understood by reference to the following detailed description in conjunction with the attached drawings, in which:

FIG. 3 is a perspective view of another embodiment of a suture in accordance with the present disclosure;

FIG. 4A-4H are various embodiments of extensions in accordance with the present disclosure;

FIGS. 5A-5B are perspective views on another embodiment of a suture in accordance with the present disclosure;

FIG. 5C illustrates a cross-sectional view of FIG. 5B taken along line X-X;

DETAILED DESCRIPTION

Figure 1A:
FIGS. 1A-1M are various end effectors in accordance with certain embodiments of the present disclosure.
Figure 1B:
Figure 1C:
Figure 1D:
Figure 1E:
Figure 1F:
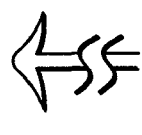
Figure 1G:
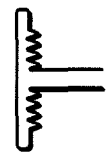
Figure 1H:
Figure 1I:
Figure 1J:
Figure 1K:
Figure 1L:
Figure 1M:

The present disclosure describes sutures including a first elongate body having first connection structure, and a second elongate body which is selectively connectable to the first connection structure. In some embodiments, the second elongate body may include a second connection structure.

The term "suture" as used herein is broadly defined as a medical device which may be used to approximate tissues during wound healing. Sutures described herein may include at least one needle disposed at an end portion of the first or second elongate body.

Sutures of the present disclosure may be provided with materials comprising both absorbable and non-absorbable materials. As used herein, the term "absorbable" includes both biodegradable and bioresorbable materials. By biodegradable, it is meant that the materials decompose, or lose structural integrity under body conditions (e.g., enzymatic degradation, hydrolysis) or are broken down (physically or chemically) under physiologic conditions in the body (e.g., dissolution) such that the degradation products are excretable or absorbable by the body.

Suitable absorbable materials include those selected from the group consisting of polymers selected from the group consisting of aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly (hydroxybutyric acid), poly(hydroxyvaleric acid), and poly (hydroxybutyrate); polyimide carbonates; poly(imino carbonates) such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide)bioabsorbable polymers; and copolymers, block copolymers, homopolymers, blends, and combinations thereof.

More specifically, for the purpose of this invention, aliphatic polyesters include, but are not limited to, homopolymers and copolymers of lactide (including lactic acid, D-, L-and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α, α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof. In certain embodiments, the mesh may comprise an aliphatic polyester.

Other suitable biodegradable polymers include, but are not limited to, poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Suitable non-absorbable materials which may be employed in the present disclosure include those such as polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers and copolymers, such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins, such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

In certain embodiments, both absorbable and non-absorbable materials may be employed in the suture. For example, a non-absorbable first elongate body may be provided with an absorbable second elongate body.

It should be noted that sutures of the present disclosure include both monofilament and multifilament sutures. In certain embodiments sutures may have a first elongate body which comprises a multifilament braid while a second elongate body may comprise a monofilament. Various combinations of multifilaments, monofilaments and absorbable and non-absorbable materials may be employed in the present disclosure. Further, sutures of the present disclosure may include at least one needle attached to at least one end thereof. Suitable needles include those within the purview of those skilled in the art.

Methods for forming sutures in accordance with the present disclosure include techniques within the purview of those skilled in the art, such as, for example, extrusion, molding and/or solvent casting. In some embodiments, the suture may include a yarn made of more than one filament, which may contain multiple filaments of the same or different materials. Where the suture is made of multiple filaments, the suture may be made using any known technique such as, for example, braiding, weaving or knitting. The suture may also be combined to produce a non-woven suture. The suture may be drawn, oriented, crinkled, twisted, commingled or air entangled to form yarns as part of the suture forming process. In one embodiment, a multifilament suture may be produced by braiding. The braiding may be done by any method within the purview of those skilled in the art.

Further, sutures described herein may be of any suitable cross-sectional shape, for example, elliptical, square, star shaped, octagonal, rectangular, polygonal and flat.

In certain embodiments, sutures described herein may comprise barbed sutures. The first or second elongate bodies may comprise a plurality of barbs disposed on a portion of a length thereof. In certain embodiments, both the first and second elongate bodies may comprise a plurality of barbs. Sutures of the present disclose may comprise both monodirectional and bidirectional barbed sutures.

Bidirectional barbed sutures include barbs which may be arranged on a first portion of a length of the first elongate body to allow movement of a first end of the elongate body through tissue in one direction, while barbs on a second portion of a length of the second elongate body may be arranged to allow movement of the second end of the elongate body in an second (e.g., opposite) direction.

Suitable barbed sutures include those described in US. Patent Publication Nos. 2009/0210006 and 2009/0248070 both assigned to Tyco Healthcare Group LP (North Haven, Conn.), the entire contents of which are incorporated by reference herein. In general, barbed sutures include barbs which extend outward, from a surface of the suture. The barbs may be disposed on a length of the medical device body (suture) to allow movement of a first end of the medical device through tissue in one direction, while resisting movement in the opposite direction.

The barbs can be arranged in any suitable pattern, for example, helical, spiral, linear, or randomly spaced. The pattern may be symmetrical or asymmetrical. The number, configuration, spacing and surface area of the barbs can vary depending upon the tissue in which the suture is used, as well as the composition and geometry of the material utilized to form the suture. Additionally, the proportions of the barbs may remain relatively constant while the overall length of the barbs and the spacing of the barbs may be determined by the tissue being connected. For example, if the suture is to be used to connect the edges of a wound in skin or tendon, the barbs may be made relatively short and more rigid to facilitate entry into this rather firm tissue. Alternatively, if the suture is intended for use in fatty tissue, which is relatively soft, the barbs may be made longer and spaced further apart to increase the ability of the suture to grip the soft tissue.

The surface area of the barbs can also vary. For example, fuller-tipped barbs can be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. In particular embodiments, a barbed suture may have both large and small barbs.

Sutures of the present disclosure may additionally include an end effector. End effectors provide resistance to help prevent the suture from being pulled through tissue. Often the end effector may be used in place of a surgeon tying a knot at one end of the suture line. End effectors may be larger in cross-sectional diameter (compared to the elongate body) so that suture pull through is prevented. In other embodiments, end effectors are sized and shaped so as to mitigate suture pull through. Examples of suitable end effectors include a knotted end effector such as one described in U.S. Publication No. 2010/0094337, filed on Oct. 1, 2009, the entire contents of which are incorporated by reference. Another suitable end effector comprises a loop at a distal portion of the suture, the loop is described in U.S. Publication No. 2010/0063540, filed on Aug. 29, 2009, the entire contents of which are incorporated by reference herein.

Other suitable end effectors which may be utilized in accordance with the present disclosure are illustrated in FIGS. 1A-1M. It should be understood that end effectors in accordance with the present disclosure are not limited to those described herein and other end effectors may be employed.

Figure 2A:
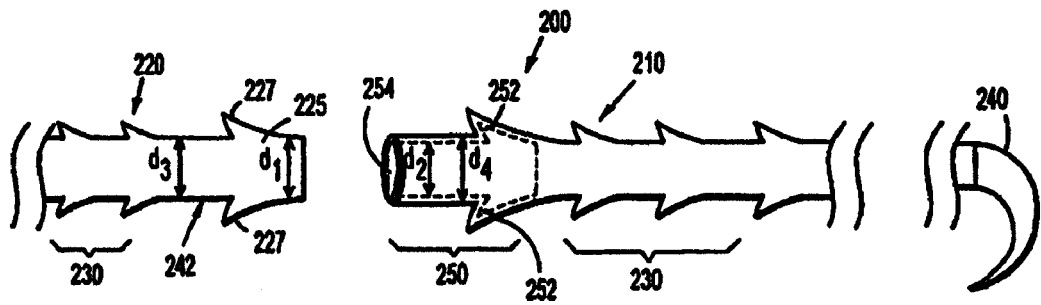
FIGS. 2A-2D are perspective views of one embodiment of a suture in accordance with the present disclosure.
Figure 2B:
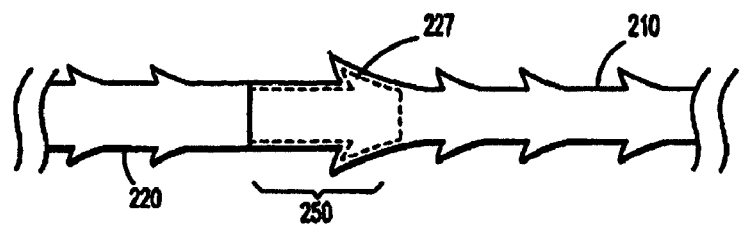

One example of a suture in accordance with the present disclosure is illustrated in FIGS. 2A and 2B. The suture 200 includes a first elongate body 210 and a second elongate body 220. As illustrated, both the first and second elongate bodies, 210, 220 include a plurality of barbs 230 disposed on a length thereof. The plurality of barbs 230 extend in the same direction, outward and away from a surface of the elongate body. As illustrated, the barbs 230 extend away from a proximal portion of the suture. A first portion of the first elongate body includes a needle 240 and a second portion of the first elongate body 210 includes a first connection structure 250. As shown herein, the first connection structure 250 includes a cavity 254 comprising at least two pockets 252. The first connection structure 250 matingly cooperates with the second elongate body 220.

The second elongate body 220 includes a proximal portion 242 having an extension 225 and at least two tabs 227. The extension 225 is shaped to be received within the distal portion of the elongate body 210. More specifically, the tabs 227 are shaped to be received within the pockets 252 (FIG. 2A). An outer diameter $d_1$ of the extension 225 is less than an inner diameter $d_2$ of the cavity 254 such that the extension 225 can be inserted within cavity 254. The first elongate body 210 comprises an outer diameter $d_4$ which is greater than $d_2$. The second elongate body also comprises a second outer diameter $d_3$, which may be greater than $d_1$. In other embodiments, $d_1$ and $d_3$ may be of similar size and both less than $d_2$.

In some embodiments, the pockets 252 and the tabs 227 form an irreversible connection. Once connected, the configuration of the pockets 252 and tabs 227 prevent the second elongate body 220 from being removed or disconnected from the elongate body 210.

Once connected, the first and second elongate bodies 210, 220 create a monodirectional barbed suture. The barbs 230 on the first and second elongate bodies 210, 220 are arranged to enable the suture to move in one direction. The barbs 230 extend away from the elongate bodies 210, 220 and away from the needled end of the suture 200.

Figure 2C:
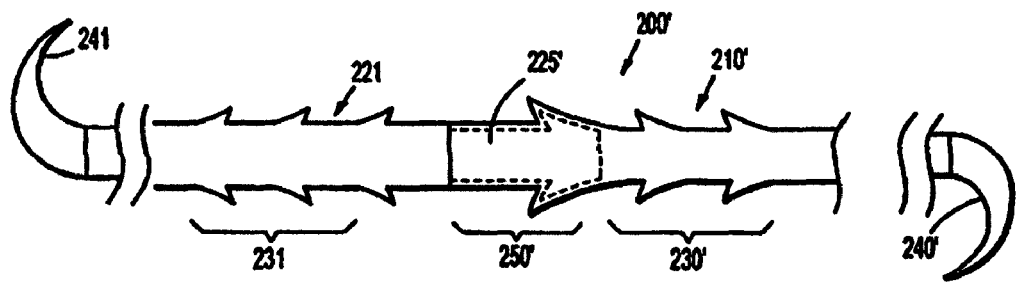

It will be understood that FIG. 2C is a similar embodiment to FIG. 2A and therefore all numerals and descriptions which are the same are designated with the prime mark and the differences will be described below. FIG. 2C illustrates a suture 200' having first and second elongate bodies 210', 221, respectively. The first elongate body 210' comprises a first needle 240' disposed at one end thereof. Additionally, the second elongate body 221 comprises a second needle, 241, disposed at one end thereof. The first elongate body 210' includes a first plurality of barbs 230' which extend outward from the first elongate body 210' in a first direction and away from the needle 240'. The second elongate body 221 includes a second plurality of barbs 231, which extend outward from the second elongate body 221 in a second direction, away from the second needle 241. The combination of the first and second plurality of barbs 230', 231, respectively, creates a bidirectional barbed suture.

Figure 2D:
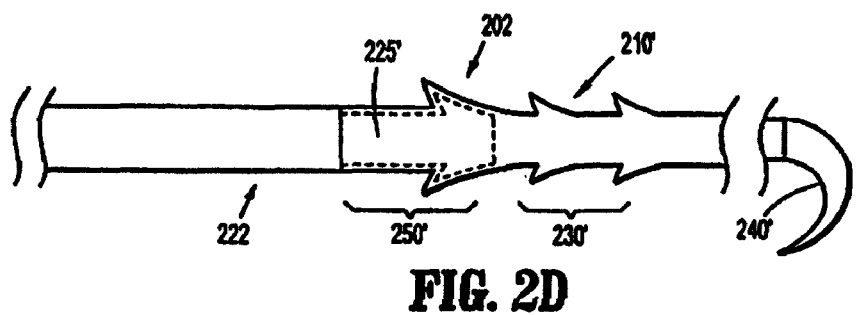

FIG. 2D is a similar embodiments to FIG. 2A and therefore all numerals and descriptions which are the same are designated with the prime mark and the differences will be described below. FIG. 2D illustrates a suture 202 having first and second elongate bodies 210', 222, respectively. The first elongate body 210' comprises a first needle 240' disposed at one end thereof. The first elongate body 210' includes a plurality of barbs 230' which extend in a first direction, outward from the elongate body 210' and away from the needle 240'. The second elongate body 222 comprises a monofilament thread. The two elongate bodies are connected together by the extension 225' and the first connection structure 250'. Although not shown, the second elongate body 222 may include a second needle disposed at one end thereof.

FIG. 3 illustrates another example of a suture 300 having a first elongate body 310 and a second, separately connectable elongate body 320, in accordance with the present disclosure. An end of one or both of the elongate bodies 310, 320 may be configured for needle attachment. Various needles for use are within the purview of those skilled in the art. The distal portion of the first elongate body 310 includes a first connection structure 340. Similar to FIG. 2A, the first connection structure 340 includes a cavity 344 which enables insertion of an extension 325. Additionally, the first connection structure 340 also includes slot 346, extending from the outer surface 310a of the first elongate body 310 to the cavity 344 of the first elongate body. The slot 346 is sized and shaped for reception of a projection 327 from the surface of the second elongate 320.

More specifically, the second elongate body 320 includes a distal portion and a proximal portion. The proximal portion includes an extension 325 and at least one projection 327 formed on a surface thereof. The extension 325 is shaped to be received within the cavity 344 of the first connection structure 340. More specifically, the projection 327 is shaped to be received within the slots 346 (on distal portion of the first elongate body 310a). In some embodiments, the slots 346 and the projections 327 form a snap fit or a friction fit. Once connected, the snap fit feature of the slots 346 and the projections 327 prevent the second elongate body 320 from being removed or disconnected from the elongate body 310.

The projections (found on extension 325) may be a variety of shapes, including but not limited to those illustrated in FIGS. 4A-4H. The projections may extend from at least one surface of the extension such as those illustrated in FIGS. 4A-4D. For example, FIG. 4A is illustrated as extending outward from a first surface of the extension 325a, while FIGS. 4E-4H illustrate projections extending outward from a first and second surface 325a, 325b, respectively of the extension 325.

For exemplary purposes, FIGS. 5A-C illustrates in more detail, how an extension similar to that illustrated in FIG. 4G connects with a first elongate body. The suture 400 is illustrated having a first elongate body 410 and a second, separately connectable elongate body 420. A proximal end of one or both of the elongate bodies 410, 420 may be configured for needle attachment. The distal portion of the first elongate body 410 includes a first connection structure 440, having a cavity 444 which enables insertion of an extension 425. Additionally, the first connection structure 440 also includes two slots 446a, 446b, each extending from an outer surface 410a of the first elongate body 410 to the cavity 444 of the first elongate body 410 (see FIG. 5C). Each slot 446a, 446b is sized and shaped for reception of a projection 427 from the surface of the second elongate 320.

More specifically, the second elongate body 420 includes a distal portion and a proximal portion. The proximal portion includes an extension 425 and at least one projection 427 formed on a surface of the extension 425. Upon insertion of the extension 425 into the cavity 444, the projections 427 may bend or fold (FIG. 5A) towards the second elongate body 420 to enable insertion of the projections 427 in the direction shown in arrow A. Once the projections 427 reach the slots 426a, 426b, the projections 427 extend outward to a second, unfolded position (see FIG. 5B), preventing removal of the extension 425 from the cavity 444.

In certain embodiments, both the first and second elongate bodies include first and second connection structures. Connection structures in accordance with the present disclosure are discussed herein below and may include a ball connection, a socket connection, a snap-fit connection, a threaded connection, and a flared connection.

Figure 6A:
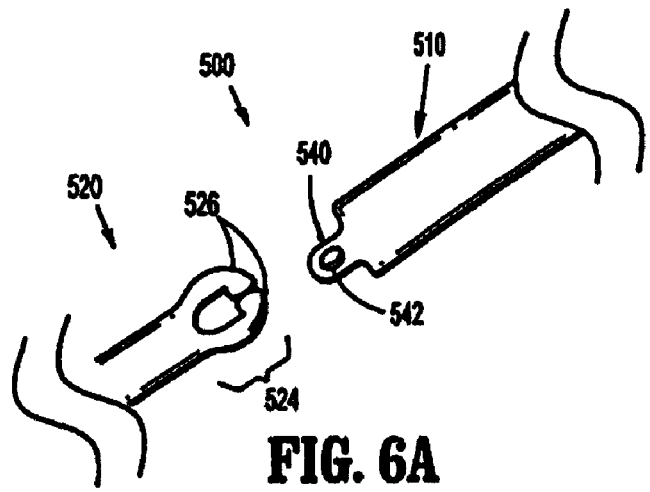
FIGS. 6A-6B are perspective views of another embodiment of a suture in accordance with the present disclosure.
Figure 6B:
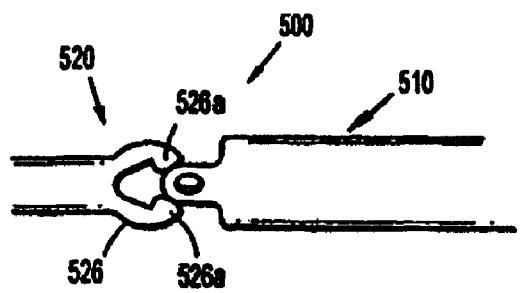
Figure 6C:
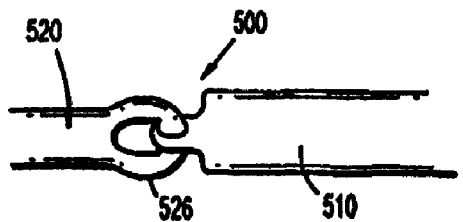
FIG. 6C is a side view of the suture of FIG. 6A in accordance with the present disclosure.

FIGS. 6A-6C illustrate an alternate embodiment of a suture in accordance with the present disclosure, including both first and second connection structures. More particularly, the suture 500 includes a first elongate body 510 and a second elongate body 520. A proximal end of the elongate body may include a needle (not shown) and a distal portion of the first elongate body 510 includes a first connection structure 540. The first connection structure 540 includes a hole or perforation 542, which is shaped and sized to receive a second connection structure.

More specifically, the second elongate body 520 comprises a second connection structure 524 at a proximal portion of the second elongate body 520. The second connection structure 524 comprises two flexible arms 526 which slightly separate as the arms 526 are moved into communication with the hole 542 (FIG. 6B). The arms 526 each comprise a bulbous portion 526a which slides across the first connection structure 540 until the hole 542 is reached. Once the bulbous portions 526a reach the hole 542, the bulbous portions 526a slide into the hole 542 and the arms 526 return to their original, unflexed position (FIG. 6C).

Figure 7:
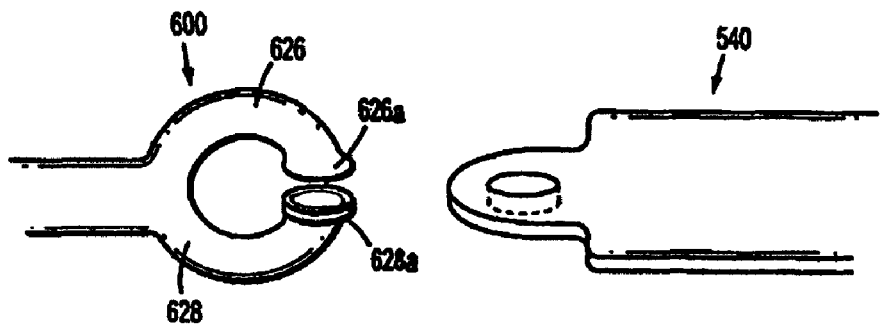
FIG. 7 is another embodiment of a second connection member in accordance with the present disclosure.

The first connection structure 540 can also be used with a different second connection structure, such as, for example, one illustrated in FIG. 7. The second connection structure 600 shown in FIG. 7 includes two arms 626, 628, respectively. The first arm 626 terminates in a bulbous portion 626a. The second arm 628 terminates in a recess configuration 628a which is shaped and sized to receive the bulbous portion 626a. The second connection structure 600 functions in a similar manner as the second connection structure 524 (FIGS. 6A-6C). In some embodiments, the arms are flexible and slightly separate as they are moved into communication with the hole on a first connection structure 540. Once the two arms 626, 628 reach the hole, the first arm 626 is received within the hole and connects to the second arm 628. More specifically, the bulbous portion 626a is received within the recess configuration 628a. The two arms 626, 628 may require a small manual force to be connected together. As shown, the first and second arms 626, 628, create a snap fit connection. In some embodiments, the snap fit connection may be reversible.

Figure 8:
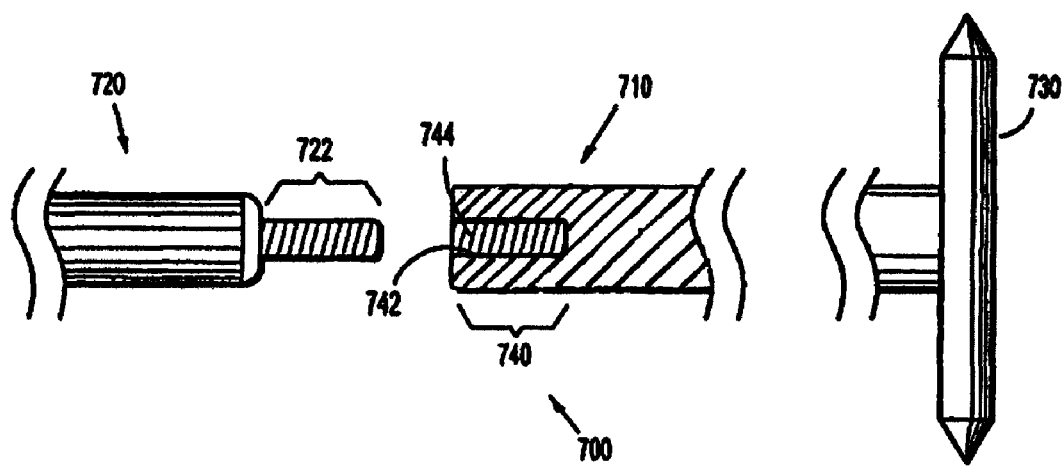
FIG. 8 is a cross-sectional view of an alternate embodiment of a suture in accordance with the present disclosure; and, FIGS. 9A-9B illustrate perspective views of another embodiment of a suture in accordance with the present disclosure.

An alternative embodiment of first and second connection structures are illustrated in FIG. 8. The suture 700 includes a first elongate body 710 and a second elongate body 720. A proximal end of the first elongate body includes a needle 730 and a distal portion of the first elongate body 710 includes a first connection structure 740. As shown herein, the first connection structure 740 has an interior concentric threaded portion 742. The concentric threaded portion 742 surrounds a cavity 744 in the distal portion of the elongate body 710. The cavity 744 enables insertion of a second connection structure 722 into the elongate body 710.

The second elongate body 720 may include a distal portion (not shown) which is shaped to mitigate suture pull through. A proximal portion of the second elongate body 710 includes a second connection structure 722 which comprises a threaded extension 722. The threaded extension 722 is shaped to be received within first connection structure 740 and more particularly, within the cavity 744. The threaded extension 722 may comprise a right-handed or left-handed thread, corresponding to the threaded portion 742 of the first connection structure 740. The extension 722 is threaded within the first connection structure 740, creating a reversible connection. In other embodiments, however, the threaded connection may be configured to be irreversible.

Figure 9A:
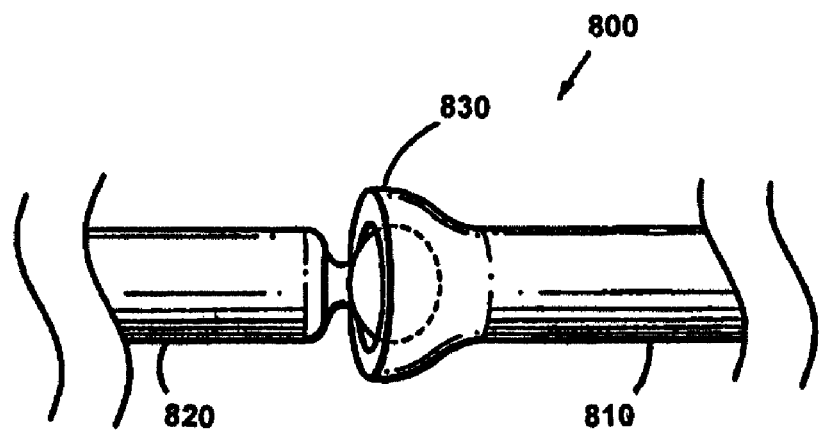
Figure 9B:
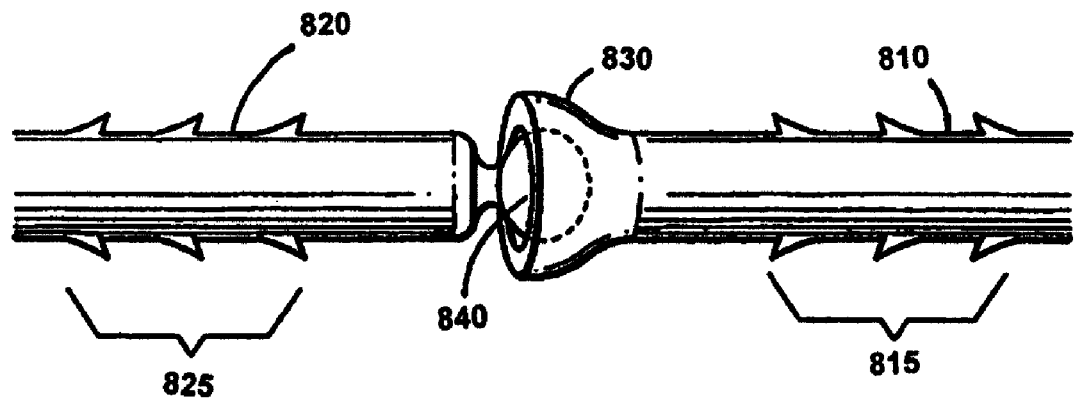

FIGS. 9A and 9B illustrate a suture in accordance with an alternate embodiment of the present disclosure. The suture 800 includes a first elongate body 810, having a first connection structure 830, and a second elongate body 820, having a second connection structure 840. The first connection structure 830 comprises a flange-shaped socket located at a first end of the first elongate body 810. The second connection structure 840 comprises a ball located at a first end of the second elongate body 820. The ball 840 is shaped to be received within the socket 830. Once the ball 840 is inserted into the socket 830, the socket 830 may be crimped or otherwise compressed to fully encompass and contain the ball therein (FIG. 9B). The ball 840 is free to rotate within the socket 830.

Further, the first elongate body 810 includes a plurality of barbs 815 located on a surface of the suture, the plurality of barbs extending in a first direction. The second elongate body 820 includes a second plurality of barbs 825 located on a surface of the suture, the second plurality of barbs 825 extending in a second direction. Once the connection is made between the first elongate body and the second elongate body, a bidirectional barbed suture is created.

The elongate bodies described herein may be connected to one another during manufacturing or even in the operating room. For example, by connecting the elongate bodies during manufacturing, several combinations of sutures can be created and packaged. For example, a barbed elongate body can be connected to an unbarbed elongate body. In another non-limiting example, a monofilament elongate body can be connected to a multifilament elongate body. Several combinations and different suture lengths can be created using multifilament and monofilament barbed and unbarbed elongate bodies. It is also envisioned that more than two elongate bodies can be connected together. For example, one elongate body may include a connection structure disposed at each end. In one example an unbarbed elongate body can be connected at each end to a barbed elongate body. The two barbed elongate bodies may comprise barbs which are angled in different directions, therefore creating a bidirectional barbed suture with an unbarbed elongate body disposed between the barbed elongate bodies.

Another alternative is to have the surgeon choose and connect the various elongate bodies, specific to the patient or procedure, in the operating room. For example, a suture kit may be provided having several elongate bodies. The surgeon may create a suture by connecting the separate elongate bodies together, utilizing the connection structures and extension provided.

Further, sutures may additionally include coatings for improved performance/handling characteristics, suitable coatings are within the purview of those skilled in the art.

In certain embodiments, sutures described herein may include at least one therapeutic agent. The term "therapeutic agent," as used herein, is used in its broadest sense and includes any substance or mixture of substances that provides a beneficial, therapeutic, pharmacological, and/or prophylactic effect. The agent may be a drug which provides a pharmacological effect.

The term "drug" is meant to include any agent capable of rendering a therapeutic effect, such as, anti-adhesives, anti-microbials, analgesics, antipyretics, anesthetics (e.g. local and systemic), antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of agents may be used.

Other therapeutic agents, which may be included as a drug include: anti-fertility agents; parasympathomimetic agents; psychotherapeutic agents; tranquilizers; decongestants; sedative hypnotics; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; and immunological agents.

Other examples of suitable agents, which may be included in the sutures described herein include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (e.g., IL-2, IL-3, IL-4, IL-6); interferons (e.g., β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, and RNAi; oligonucleotides; polynucleotides; and ribozymes.

Some specific non-limiting examples of water-soluble drugs that may be used in the present disclosure include, lidocaine, bupivicaine, tetracaine, procaine, dibucaine, sirolimus, taxol, chlorhexidine, polyhexamethylene, thiamylal sodium, thiopental sodium, ketamine, flurazepam, amobarbital sodium, phenobarbital, bromovalerylurea, chloral hydrate, phenytoin, ethotoin, trimethadione, primidone, ethosuximide, carbamazepine, valproate, acetaminophen, phenacetin, aspirin, sodium salicylate, aminopyrine, antipyrine, sulpyrine, mepirizole, tiaramide, perixazole, diclofenac, anfenac, buprenorphine, butorphanol, eptazocine, dimenhydrinate, difenidol, dl-isoprenaline, chlorpromazine, levomepromazine, thioridazine, fluphenazine, thiothixene, flupenthixol, floropipamide, moperone, carpipramine, clocapramine, imipramine, desipramine, maprotiline, chlordiazepoxide, clorazepate, meprobamate, hydroxyzine, saflazine, ethyl aminobenzoate, chlorphenesin carbamate, methocarbamol, acetylcholine, neostigmine, atropine, scopolamine, papaverine, biperiden, trihexyphenidyl, amantadine, piroheptine, profenamine, levodopa, mazaticol, diphenhydramine, carbinoxamine, chlorpheniramine, clemastine, aminophylline, choline, theophylline, caffeine, sodium benzoate, isoproterenol, dopamine, dobutamine, propranolol, alprenolol, bupranolol, timolol, metoprolol, procainamide, quinidine, ajmaline, verapamil, aprindine, hydrochlorothiazide, acetazolamide, isosorbide, ethacrynic acid, captopril, enalapril, delapril, alacepril, hydralazine, hexamethonium, clonidine, bunitrolol, guanethidine, bethanidine, phenylephrine, methoxamine, diltiazem, nicorandil, nicametate, nicotinic-alcohol tartrate, tolazoline, nicardipine, ifenprodil, piperidinocarbamate, cinepazide, thiapride, dimorpholamine, levallorphan, naloxone, hydrocortisone, dexamethasone, prednisolone, norethisterone, clomiphene, tetracycline, methyl salicylate, isothipendyl, crotamiton, salicylic acid, nystatin, econazole, cloconazole, vitamin $B_1$, cycothiamine, vitamin $B_2$, vitamin $B_3$, vitamin $B_5$, vitamin $B_6$, vitamin $B_7$, vitamin $B_9$, vitamin $B_{12}$, vitamin C, nicotinic acid, folic acid, nicotinamide, calcium pantothenate, pantothenol, panthetin, biotin, ascorbic acid, tranexamic acid, ethamsylate, protamine, colchicine, allopurinol, tolazamide, glymidine, glybuzole, metoformin, buformin, orotic acid, azathioprine, lactulose, nitrogen mustard, cyclophophamide, thio-TEPA, nimustine, thioinosine, fluorouracil, tegafur, vinblastine, vincristine, vindesine, mitomycin C, daunorubicin, aclarubicin, procarbazine, cisplatin, methotrexate, benzylpenicillin, amoxicillin, penicillin, oxycillin, methicillin, carbenicillin, ampicillin, cefalexin, cefazolin, erythromycin, kitasamycin, chloramphenicol, thiamphenicol, minocycline, lincomycin, clindamycin, streptomycin, kanamycin, fradiomycin, gentamycin, spectinomycin, neomycin, vanomycin, tetracycline, ciprofloxacin, sulfanilic acid, cycloserine, sulfisomidine, isoniazid, ethambutol, acyclovir, gancyclovir, vidabarine, azidothymidine, dideoxyinosine, dideoxycytosine, morphine, codeine, oxycodone, hydrocodone, cocaine, pethidine, fentanyl, polymeric forms of any of the above drugs and any combinations thereof.

Therapeutic agents may be combined with sutures in various forms. For example, therapeutic agents may be combined with the sutures in the form of a coating. Suitable methods for coating sutures are within the purview of those skilled in the art and include, but are not limited to, spray coating, dip coating, extrusion, coextrusion, overmolding, and the like. Additionally, the therapeutic agent may be combined with polar and non-polar solvents creating a suture coating.

Therapeutic agent may also be polymerized off the surface of the suture or compounded within the polymer resin used to create the suture. In other embodiments, polymer drugs (e.g., polydiflunisol, polyaspirin, and protein therapeutics) may be utilized to create sutures of the present disclosure.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, the disclosure is not limited to those embodiments described herein and various combinations of elongate bodies, with and without barbs may be combined, including monofilament and multifilament configurations. Additionally needles may be disposed at one or both ends of the suture.

What is claimed is:

1. A suture comprising:
    a first length of suture having proximal and distal portions and a first connection structure, wherein the first connection structure includes a cavity defined in the distal portion and at least a first recess spaced proximal of a distal end of the distal portion in communication with the cavity; and
    a separate second length of suture selectively connectable to the first connection structure and including an extension and at least one projection extending radially outward from the extension, wherein the at least one projection is configured to extend into the at least first recess in the distal portion of the first length of suture when the extension is received within the cavity of the distal portion.

2. The suture according to claim 1, wherein upon the receipt of the at least one projection through the at least one recess, separation of the second length of suture from the first length of suture is prevented.

3. The suture according to claim 1, wherein the first or second length of suture comprises an end effector.

4. The suture according to claim 3, wherein the end effector is selected from the group consisting of a loop and a knot.

5. The suture according to claim 1, wherein first or second length of suture comprises a needle disposed at one end thereof.

6. The suture according to claim 1, wherein the first and second length of suture each comprise a needle disposed at one end thereof.

7. The suture according to claim 1, wherein the first or second length of suture further comprises barbs disposed on a length thereof.

8. The suture according to claim 1, wherein the at least first recess includes a notch and the at least first projection includes a barb.

9. The suture according to claim 1, wherein the at least first recess includes first and second notches and the at least first projection includes first and second barbs.

10. The suture according to claim 1, wherein the at least first recess includes a slot and the at least first projection is configured to be received through the slot.

11. A suture comprising at least two separately connectable lengths of suture, wherein a first length of suture comprises an end portion including a first connection structure that is connectable to a second connection structure of a second length of suture, wherein the first connection structure defines a perforation and the second connection structure includes a pair of arms each having a bulbous end portion configured for reception within the perforation of the first connection.

12. The suture according to claim 11, wherein the first length of suture comprises a first plurality of barbs.

13. The suture according to claim 12, wherein the first plurality of barbs prevents suture reversal in a first direction.

14. The suture according to claim 11, wherein the second length of suture comprises a second plurality of barbs.

15. The suture according to claim 14, wherein the second plurality of barbs prevents suture reversal in a second direction.

16. The suture according to claim 11, wherein the pair of arms is configured to flex away from each other to facilitate reception of the bulbous end portions within the perforation.

* * * * *